(12) United States Patent
Guo et al.

(10) Patent No.: US 9,207,159 B2
(45) Date of Patent: Dec. 8, 2015

(54) PARTICLE ANALYZER FOR ANALYZING PARTICLES

(75) Inventors: Wenheng Guo, Shenzhen (CN); Jin Teng, Shenzhen (CN); Yingjian Zhan, Shenzhen (CN); Shuang Zhou, Shenzhen (CN); Huilin Shi, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 242 days.

(21) Appl. No.: 13/326,188

(22) Filed: Dec. 14, 2011

(65) Prior Publication Data
US 2012/0171659 A1    Jul. 5, 2012

(30) Foreign Application Priority Data
Dec. 31, 2010 (CN) .......................... 2010 1 0619709

(51) Int. Cl.
*G01N 33/00* (2006.01)
*G01N 31/00* (2006.01)
(Continued)

(52) U.S. Cl.
CPC ................ *G01N 15/14* (2013.01); *G01N 35/00* (2013.01); *G01N 2015/1486* (2013.01)

(58) Field of Classification Search
CPC .......... G01N 35/00; G01N 2015/0084; G01N 15/14; G01N 15/1404; G01N 15/1456; G01N 15/1463; G01N 15/147; G01N 1/14; G01N 2015/0069; G01N 2015/0073; G01N 2015/0076; G01N 2015/008; G01N 2015/0088; G01N 2015/1037; G01N 2015/1062; G01N 2015/1413; G01N 2015/1477; G01N 2015/1486; G01N 2035/00356; G01N 2035/00524; G01N 2035/1032; G01N 21/47; G01N 21/64; G01N 33/493; G01N 35/0092; G01N 35/10; G01N 35/1004; G01N 35/109; G01N 35/1095
USPC .................................................. 422/73, 930
See application file for complete search history.

(56) References Cited

U.S. PATENT DOCUMENTS 4,667,335 A    5/1987 Deindoerfer
5,939,326 A *  8/1999 Chupp et al. .................... 436/43
(Continued)

FOREIGN PATENT DOCUMENTS

CN    1727902       2/2006
CN    17181458 A    6/2006
(Continued)

OTHER PUBLICATIONS

Feng, Li-jian, "Working Principle and Performance Testing of Oxygen Battery in Ventilator," Equipment Department, the First Hospital of Ninghai, County, Ningbo Zhejiang, 315600, Chin, Nov. 4, 2008, pp.
(Continued)

*Primary Examiner* — Dean Kwak
(74) *Attorney, Agent, or Firm* — Kory D. Christensen; Stoel Rives LLP

(57) ABSTRACT

A particle analyzer may include a sampling unit configured to collect samples containing particles; a sample preparing unit configured to prepare different sub-samples; a reaction unit configured to incubate the sub-samples and one or more corresponding reagents respectively and provide them to the injecting unit; an injecting unit configured to inject the sub-samples to the optical unit; an optical unit configured to irradiate the sub-samples to obtain particle information; a processing unit configured to process and output the particle information; and a threshold value unit configured to compare a total number of particles with a pre-determined threshold value and to output a result of the comparison to the injecting unit to control subsequent injection of one or more sub-samples.

6 Claims, 3 Drawing Sheets

(51) Int. Cl.
*G01N 15/14* (2006.01)
*G01N 35/00* (2006.01)

(56) References Cited

U.S. PATENT DOCUMENTS

| 6,525,807 | B1 | 2/2003 | Morikawa et al. |
| 8,192,995 | B2 * | 6/2012 | Zhang et al. ................... 436/66 |
| 2008/0100840 | A1 | 5/2008 | Oma et al. |

FOREIGN PATENT DOCUMENTS

| CN | 101000306 | 7/2007 |
| CN | 101025414 | 8/2007 |
| CN | 101325911 A | 12/2008 |
| JP | 2002-277381 | 9/2002 |

OTHER PUBLICATIONS

Zhu, Xing-xi, et al., "Design an oxygen supply device synchronized with breath," The General Hospital of Nanjing Military Area, Nanjing Kiangsu 2100002, China, Sep. 2009, pp. 4-6.

* cited by examiner

PARTICLE ANALYZER FOR ANALYZING PARTICLES

CROSS-REFERENCE TO RELATED APPLICATIONS

This application claims the benefit of Chinese Patent Application No. 201010619709.1, filed Dec. 31, 2010, which is incorporated herein by reference in its entirety.

TECHNICAL FIELD

The following disclosure relates to sample analyzers and methods for analyzing particles.

SUMMARY OF THE INVENTION

A particle analyzer and a method for analyzing particles are disclosed.

DETAILED DESCRIPTION

In modern medical systems, there is often a need to analyze particles in body fluids (e.g., cells in blood) to obtain various parameters. The parameters may include, for example, a scatter diagram of total particles and/or certain particles. A particle analyzer for analyzing and counting blood cells or other body fluid cells is usually called a cell analyzer.

Figure 1:
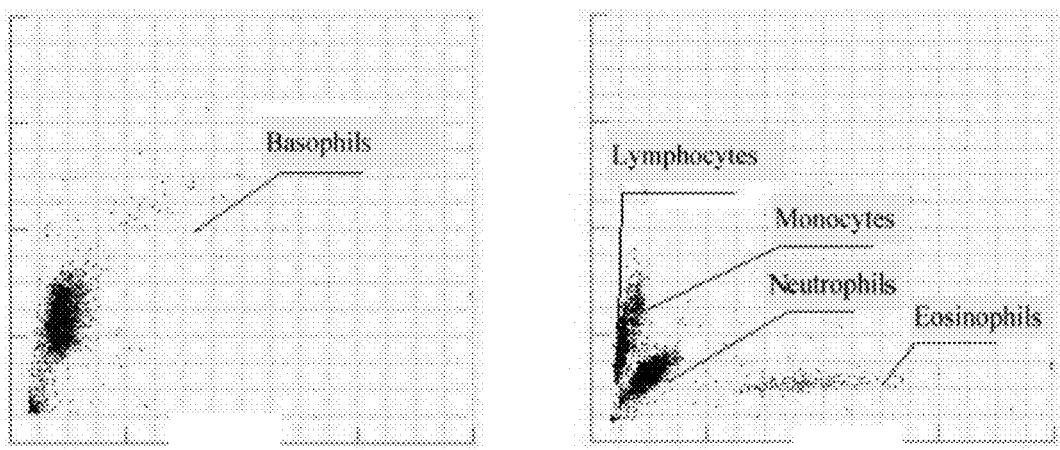
FIG. 1 is a typical scatter diagram for total white blood cells and classified cells.

White blood cells, for example, can usually be classified into five basic groups: neutrophils, lymphocyte, monocytes, eosinophils, and basophils. Classifying these cells and reporting their relative percentages among the total white cells is a key index of five-part differential blood cell analyzers. These analyzers generally rely on flow cytometry. According to flow cytometry, after the cells have been processed with reagents, they pass through a flow chamber one by one while being driven by a syringe. Every cell is exposed to laser light to generate information. As shown in FIG. 1, the information for all of the cells may be displayed in a coordinate graph to form a scatter diagram, each point in the scatter diagram representing a cell. The left drawing of FIG. 1 is for the total white blood cells, and the right drawing of FIG. 1 is for white blood cell classification.

The total number of white blood cells is usually counted first from a scatter diagram of the total white blood cells while a percentage of the neutrophils is obtained. Thereafter, the other four groups of cells are measured and classified.

Currently, counting the white blood cells is based on a fixed volume, such as using a syringe to inject a fixed volume of a sample fluid (i.e., the volume of the syringe is fixed). Thus, for low concentration white blood cell samples, the number of cells counted would be less for the same sample volume. For example, the syringe injects a 50 μL sample, and 40 μL out of the 50 μL sample is to be counted. If a dilution ratio is 50, then a blood cell sample of 40/50=0.8 is counted. For a white blood cell sample whose concentration is 6000 per μL, as many as 4800 white blood cells are counted. However, for a white blood cell sample of a concentration of 1000 per μL, only 800 white blood cells are counted. Therefore, the accuracy of cell counting and classifying is affected. Conventional techniques for counting and classifying white blood cells are insufficient to count low concentration white blood cell samples because of the fixed injection volume. The actual cell totals counted are very small, which decreases the counting accuracy.

This disclosure provides a particle analyzer and a method for analyzing particles that overcome the above-mentioned deficiencies.

According to one embodiment, a particle analyzer includes a sampling unit, a sample preparing unit, a reaction unit, a threshold value unit, an injecting unit, an optical unit, and a processing unit. The sampling unit may be used for collecting samples containing particles. The sample preparing unit may be used for preparing different sub-samples for different purposes. The reaction unit may be used for incubating the sub-samples and corresponding reagents respectively and providing treated sub-samples to the injecting unit. The injecting unit may be used for injecting the treated sub-samples to the optical unit. The optical unit may be used for irradiating the treated sub-samples to obtain particle information. The processing unit may be used for processing and outputting the particle information. The threshold value unit may be used for comparing a total number of particles with a pre-determined threshold value and outputting a result of the comparison to the injecting unit.

In one embodiment, the sample preparing unit of the particle analyzer may be used for preparing sub-samples for counting the total number of particles and sub-samples for particle classification.

In one embodiment, the injecting unit injects the sub-sample for counting the total number of particles in a pre-determined volume, and injects a sub-sample for particle classification according to a result of comparing the total number of particles of the sub-sample with a threshold value. When a total number of the particles is not less than the threshold value, the injecting unit injects the sub-sample in a first injecting volume, and when a total number of the particles is less than the threshold value, the injecting unit injects the sub-sample in a second injecting volume. In one embodiment, the first injecting volume is less than the second injecting volume.

In various embodiments, the sample may be a blood sample, and the particles may be white blood cells. The processing unit, in some embodiments, may output scatter diagrams.

In one embodiment, the injecting unit may employ a motor to drive the injecting unit to inject the first injecting volume or the second injecting volume by controlling a speed and/or driving time of the motor.

According to one embodiment, a method for analyzing particles includes collecting a sample of particles; preparing a sub-sample according to the sample; incubating the prepared sub-sample; counting a total number of particles of the sub-sample; comparing the total number of the particles with a pre-determined threshold value; injecting a volume of the sub-sample according to the results of the comparison; and classifying the particles.

In one embodiment, the process of collecting a sample includes using a sampling unit to collect body fluid having particles. Preparing a sub-sample according to the sample includes preparing different sub-samples for different purposes. Incubating the prepared sub-sample includes uniformly mixing a sub-sample and corresponding regent. Counting a total number of particles of the sample includes using an optical unit to count the total number of particles. Comparing the total number of the particles with a pre-determined threshold value includes using a threshold value unit to compare the total number with the threshold value. Injecting a volume of the sub-sample according to a comparison result includes injecting a sub-sample in a first injecting volume when the total number of particles is not less than the threshold value, and injecting a sub-sample in a second injecting volume when the total number of particles is less than the threshold value. Classifying the particles includes classifying the particles according to the first or second injecting volume.

The threshold value may be pre-determined in a further embodiment, and the second injecting volume may be greater than the first injecting volume. In some embodiments, the second injecting volume is 1.5 to 6 times as large as the first injecting volume.

The particle analyzer and the method for analyzing particles of this disclosure may determine whether a sample is a low concentration sample based on a result of initially comparing a sub-sample and a threshold value. In other words, the first injecting volume is injected when the total number of particles is not less than the threshold value, and the second injecting volume is injected when the total number of particles is less than the threshold value. Therefore, the measurement accuracy of particle classification will not be decreased.

Figure 2:
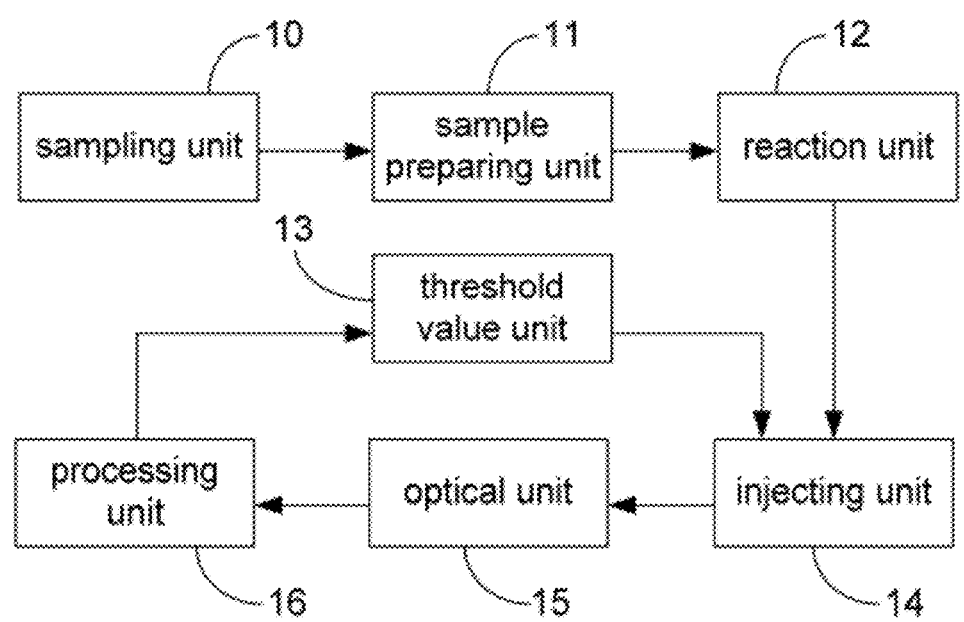
FIG. 2 is a block diagram of a particle analyzer.

Referring to FIG. 2, a particle analyzer 1 includes a sampling unit 10, a sample preparing unit 11, a reaction unit 12, a threshold value unit 13, an injecting unit 14, an optical unit 15, and a processing unit 16. The sampling unit 10 may be used for collecting samples from a body fluid into a storage container. The sample preparing unit 11 may be used for preparing the body fluid sample into different sub-samples for different purposes. The reaction unit 12 may be used for incubating the sub-samples and their corresponding reagents respectively and providing the incubated sub-samples to the injecting unit 14. The injecting unit 14 may be used for injecting the sub-samples to the optical unit 15. The optical unit 15 may be used for irradiating the sub-samples to obtain particle information. This may include, for example, a light scattering method using laser light to irradiate the body fluid cells and form forward scattering particle information and side scattering particle information. The processing unit 16 may be used for processing and outputting the particle information. The threshold value unit 13 may be used for comparing a total number of particles with a pre-determined threshold value and outputting a result of the comparison to the injecting unit 14.

In the illustrated embodiment, the body fluid sample is a blood sample, although other body fluid samples may be used. In one embodiment, the processing unit 16 outputs a scatter diagram, such as a white blood cell scatter diagram, including a diagram of the total number of white blood cells and a classification diagram. The sample preparing unit 11 may prepare a fixed 20 μL sub-sample for counting the total number of white blood cells and neutrophils, and another 20 μL sub-sample for classifying the other four groups of blood cells.

The injecting unit 14 may be preset to inject a pre-determined volume of a sub-sample for counting the total number of white blood cells, and injecting a volume for classification depending on a result of comparing the number of white blood cells and the threshold value. Because the duration of incubating the sub-sample for counting the total number of white blood cells is less than the duration for incubating the sub-sample for white blood cell classification, the sub-sample for counting the total number of white blood cells is injected before the sub-sample for white blood cell classification. When the total number of white blood cells is not less than the threshold value, the injecting unit 14 injects a first injecting volume of the sub-sample for white blood cell classification. When the total number of white blood cells is less than the threshold value, the injecting unit 14 injects a second injecting volume of the sub-sample for white blood cell classification. In one embodiment, the second injecting volume is greater than the first injecting volume. The second injecting volume may be 1.5 to 1.6 times as large as the first injecting volume. The injecting unit 14 may be driven by a motor. The threshold value may be pre-determined in the analyzer. In other embodiments, the threshold value may be set by a user through a user interface.

In one embodiment, the particle analyzer of this disclosure includes a threshold value unit 13, and the injecting volume for white blood cell classification depends on the result of comparing the total number of white blood cells and the threshold value, such that a larger volume is injected when the sub-sample is of a low concentration, which, in one embodiment, is equivalent to the total number of particles (e.g., white blood cells) being less than the threshold value. As a result, the accuracy of the particle classification can be greatly improved.

Figure 3:
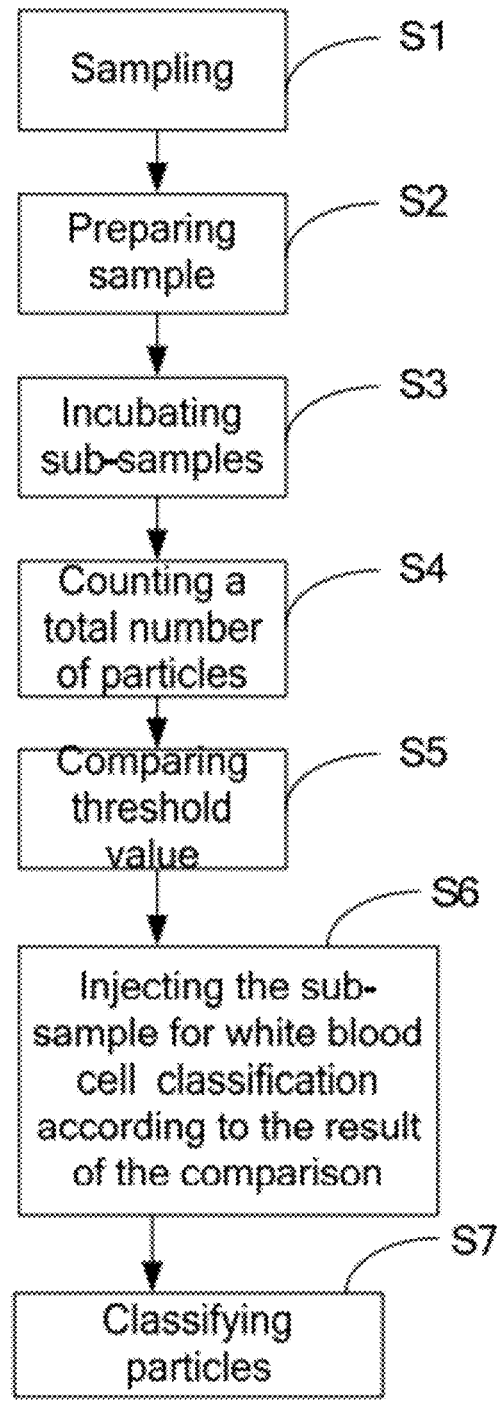
FIG. 3 is a flow diagram of a method for analyzing particles.

Referring to FIG. 3, a method for analyzing particles may include the following steps.

Step S1, sampling. The sampling unit 10 collects a body fluid that contains particles. In one embodiment, the body fluid is blood, which contains particles such as white blood cells.

Step S2, preparing sample. The sample preparing unit 11 prepares the sub-sample according to the sample collected in step S1. For example, for a blood sample, a blood dividing device, such as a shear valve, may be used to divide the blood sample into several sub-samples, which are used for different purposes. For example, 20 μL of sub-sample may be used for counting the total number of white blood cells and neutrophils, and another 20 μL of sub-sample may be used for classifying the white blood cells.

Step S3, incubating the sub-samples. The prepared sub-samples and corresponding reagents may be mixed uniformly. For example, in the reaction unit 12, (a) the sub-samples prepared in step S2 for counting white blood cells and neutrophils and for classifying white blood cells and (b) their respective specific reagents are mixed uniformly through a certain reaction duration. The reaction unit 12 may be a reaction tank.

Step S4, counting a total number of particles. For example, a mixture containing 20 μL of the sub-sample incubated in step S3 for counting white blood cells and 1 mL of a specific reagent may be injected in a certain volume into the optical unit 15 by the injecting unit 14. For example, a volume of 50 μL of treated sub-sample may be injected. In other embodiments, the volume of treated sub-sample injected into the optical unit 15 may be different according to different requirements.

Step S5, comparing the threshold value. The pre-determined threshold value is compared with the total number of particles obtained in step S4.

Step S6, injecting the sub-sample for differential white blood cell classification according to the comparison result in step S5. If the total number of particles is not less than the threshold value, then the sub-sample will be injected in a first injecting volume; otherwise, the sub-sample will be injected in a second injecting volume. In one embodiment, the second injecting volume is preferably 1.5 to 6 times as large as the first injecting volume. In the illustrated embodiment, the second injecting volume is 3 times as large as the first injecting volume. The first injecting volume is 50 μL, and the second injecting volume is 150 μL. The maximum second injecting volume will not exceed a sum of the sub-samples.

Step S7, classifying particles. Based on the injecting volume (the first injecting volume or the second injecting volume) in step S6, the particles are classified.

In one embodiment, the injecting unit 14 employs a motor to drive the injecting unit 14 to inject the first injecting volume or the second injecting volume by controlling motor speed and/or driving time.

It should be noted that the threshold value in the above-mentioned embodiments is pre-determined. However, in other or further embodiments, the threshold value can also be set and modulated by users through a user interface.

In the method for analyzing particles of this disclosure, the total number of particles is counted before the sub-sample is classified, then particle concentration of the sample is estimated by comparing the total number of particles with a pre-determined threshold value. If the total number of particles is not less than the threshold value, the sample is regarded as having normal concentration. If the total number of particles is less than the threshold value, the sample is regarded having a lower concentration. The sub-sample is injected in different injection volumes according to a different comparison result, such that the measurement accuracy of the low concentration sample is improved by injecting the sub-sample in a larger volume.

Although the present disclosure has been described with reference to the specific embodiments, such embodiments are not intended to limit the invention. Those of skill in the art can make modifications and variations without departing from the spirit and scope of the invention.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternative ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

What is claimed is:

1. A particle analyzer comprising:
   a sampling unit;
   a sample preparing unit;
   an optical unit configured;
   an injecting unit;
   a reaction unit;
   a processing unit; and
   a computer readable medium with encoded computer-executable instructions that, when executed by the processing unit, cause the processing unit to perform operations for outputting the particle information for an injection cycle, the operations comprising:
   instructing the sampling unit to collect samples containing particles;
   instructing the sample preparing unit to prepare a plurality of sub-samples;
   instructing the reaction unit to incubate the particles and one or more corresponding reagents;
   instructing the injecting unit to inject a first sub-sample having a first preset volume and a first number of particles to the optical unit;
   instructing the optical unit to irradiate the injected particles to obtain particle information associated with the particles;
   comparing the first number of particles with a pre-determined threshold value;
   outputting a result of the comparison to the injecting unit; and
   controlling a volume of a subsequent, second injection of at least a second sub-sample based on the result of the comparison, wherein the volume of the second injection is different than a second preset volume of the second sub-sample.

2. The particle analyzer according to claim 1, wherein the sample preparing unit of the particle analyzer is configured to prepare sub-samples for total particle counting and particle classification.

3. The particle analyzer according to claim 2, wherein the injecting unit injects a sub-sample for total particle counting in a pre-determined volume and injects a sub-sample for particle classification according to a result of comparing the number of particles of the sub-sample with a threshold value, and when a number of the particles is not less than the threshold value, the injecting unit injects the sub-sample in a first injecting volume, and when a number of the particles is less than the threshold value, the injecting unit injects the sub-sample in a second injecting volume, the first injecting volume being less than the second injecting volume.

4. The particle analyzer according to claim 3, wherein the injecting unit employs a motor to drive the injecting unit to inject the sub-sample in the first injecting volume or the second injecting volume by controlling a speed and/or driving time of the motor.

5. The particle analyzer according to claim 1, wherein the samples are blood samples and the particles are white blood cells.

6. The particle analyzer according to claim 1, wherein the processing unit outputs scatter diagrams.

* * * * *